United States Patent [19]

Williams

[11] Plant 5,011

[45] Mar. 29, 1983

[54] ROSE PLANT

[76] Inventor: J. Benjamin Williams, 2800 Elnora St., Silver Spring, Md. 20902

[21] Appl. No.: 282,398

[22] Filed: Jul. 13, 1981

[51] Int. Cl.[3] ..... A01H 5/00

[52] U.S. Cl. ..... Plt./11

[58] Field of Search ..... Plt./11, 18

*Primary Examiner*—Robert E. Bagwill

[57] ABSTRACT

A novel rose variety of the hybrid tea class characterized by large flowers of carmine-pink and ivory coloring, a vigorous upright growing plant with large dark green waxed foliage as shown and described herein.

1 Drawing Figure

1

The present invention relates to a new and distinct variety of rose plant of the hybrid tea class, which was originated by me by crossing two unnamed seedlings derived from crosses previously made by me of 1. "Pink Peace" (U.S. Plant Pat. No. 1,759) × "Queen Elizabeth" (U.S. Plant Pat. No. 1,259)
2. "Kordes Perfecta" (U.S. Plant Pat. No. 1,604) × "Peace" (U.S. Plant Pat. No. 591)

The primary objective of this breeding was to produce a new rose variety which combines some of the better characteristics of these outstanding roses.

This objective was fully obtained, as evidenced by the following characteristics which are outstanding in the new variety:

(1) The healthy and vigorous habit of plant growth;

(2) Its leathery and glossy dark green foliage;

(3) The distinctive and delicate blending of the basic tones of carmine pink and creamy white throughout all stages of the flower opening;

(4) The unique quartering of the large fully open flower reflects the "old rose" charm of its ancestors transmitted by the "Pink Peace" influence of this breeding; and (5) The large colorful well formed ovoid to pointed buds that are produced in large quantities throughout the growing season.

Asexual reproduction of the new variety by budding as performed at West Grove, Pa., and McFarland, Calif., shows that the foregoing characteristics and distinctions came true to form and are established and transmitted through succeeding propagations.

The accompanying drawings show typical specimens of the vegetative growth and the flowers of my new variety in different stages of development and as depicted in color as nearly true as it is reasonably possible to make the same in a color illustration of this character.

The following is a detailed description of the new variety, with color terminology in accordance with The Royal Horticultural Society Colour Chart, e.g. "RHS 55C" is reference to Color Plate 55C of The Royal Horticultural Society Colour Chart where such designation is used, except where general color terms of ordinary dictionary significance are observed.

Parentage: Seedling.

*Seed parent.*—Unnamed seedling from a cross of "Pink Peace" × "Queen Elizabeth".

*Pollen parent.*—Unnamed seedling from a cross of "Kordes Perfecta" × "Peace".

Class: Hybrid tea.

2

The following observations are made of specimens grown outdoors at Chester County, Pa., during the month of June.

FLOWER

Blooming habit: Continuous and abundant.

A. Bud:

(1) *Size.*—Large.

(2) *Form.*—Globular.

(3) *Color.*—When sepals first divide: tips RHS 53C showing ivory white base RHS 158D. When petals begin to unfurl: creamy white base with carmine pink RHS 55C blending over surface of petal. When half-blown: inside of petals — RHS 55A blending downward to 55D; reverse side of petals — cream to RHS 12C at base of attachment with carmine pink streaking two-thirds way down petal.

(4) *Sepals.*—Short and smooth extending just to tip of bud.

(5) *Peduncle.*—Length — medium 2-3". Aspect — smooth. Strength — strong and erect. Color — RHS 146B.

B. Bloom:

(1) *Size.*—Average size when fully expanded 4½ to 5 inches.

(2) *Borne.*—Singly and several together on main canes.

(3) *Form.*—High centered at first; becoming flat and ruffled at maturity. Open flower quarters giving it an old rose appearance similar in some ways to its parent "Pink Peace".

(4) *Petalage.*—Number of petals under normal conditions — 65-70.

(5) *Color.*—(During first two days) a cream and pink bicolor blend. Inner petals at center of flower — cream with light pink. Outer petals — silver white with blush to pink streaking. Base of petals (point of attachment) — ivory to light yellow near to RHS 12C. Reverse of petals — silver white to RHS 155A. General tonality from a distance — pink and cream blending similar to peppermint stick ice cream showing all shades of RHS 55A to D blended on cream near RHS 11D.

(6) *Color change.*—As bloom ages — Slight frosting of pinkish white on edge of petals. General tonality — A blending of pink RHS 55A to cream and light pink RHS 55D. After three or more days —

These colors hold well with little change after flower opens.

C. Petals:

(1) *Texture.*—Thick, not effected by wet or hot weather.

(2) *Appearance.*—Inside — velvety; outside — satiny.

(3) *Form.*—Oval.

(4) *Arrangement.*—Imbricated (regularly arranged shingle-like).

(5) *Petaloids in center.*—A number of medium to large petaloids make up quartering effect of open bloom.

(6) *Persistence.*—Drop off cleanly.

(7) *Fragrance.*—Light old rose.

(8) *Lasting quality.*—On the plant — very long. As cut flower — very long. Cut flowers and flower color improved by refrigeration.

REPRODUCTIVE ORGANS

A. Stamens, filaments and anthers:

(1) *Arrangement.*—Anthers short, bunched around styles.

(2) *Color.*—Yellow orange RHS 22C.

B. Pollen:

*Color.*—Yellow orange RHS 22A.

C. Styles: Bunched, medium length.

D. Stigmas:

*Color.*—RHS 26C.

E. Hips: None observed.

PLANT

A. Form: Upright.

B. Growth: Very vigorous; uniform branching from base of plant.

*Height attained.*—3-4 feet first season.

C. Foliage: Compound of 5 to 7 leaflets.

(1) *Size.*—Large.

(2) *Quantity.*—Abundant.

(3) *Color.*—New foliage: Upper side — RHS 138A with reddish cast. Under side — near RHS 138C.

Old foliage: Upper side — Between RHS 138A and 139A. Under side— Near RHS 137C.

(4) *Shape.*—Oval.

(5) *Texture.*—Upper side — Leathery glossy very waxed. Under side — Smooth.

(6) *Edge.*—Serrated.

(7) *Serration.*—Small and uniform from base to tip.

(8) *Leaf stem.*—Color — RHS 139C. Under side — RHS 139D.

(9) *Stipules.*—Medium length; smooth and seldom extend beyond tip of bud.

(10) *Resistance to disease.*—Blackspot — very. Mildew — very.

D. Wood:

(1) *New wood.*—Color — Light green with bronze red overcast. Bark — Smooth.

(2) *Old wood.*—Color — RHS 137C near bloom to RHS 137A at base of cane on old wood. Bark — Smooth having a waxed appearance.

E. Thorns:

(1) *Thorns.*—Quantity: on main stalks from base — only a few. On laterals from stalk — very few. Form — ovoid to flat. Length — medium. Color when young — near RHS 137C. Position — regular, slightly curved down.

(2) *Prickles.*—Quantity: on main stalks — none. On laterals — none.

F. Winter hardiness: Completely winter hardy through Zone 6.

I claim:

1. A new and distinct variety of rose plant of the hybrid tea class, substantially as shown and described, characterized as to novelty by flowers of unique carmine-pink and ivory coloring developing from large ovoid buds and borne singly and several together at times on strong stems and a very vigorous plant with large leathery glossy foliage very resistant to disease and very winter hardy.

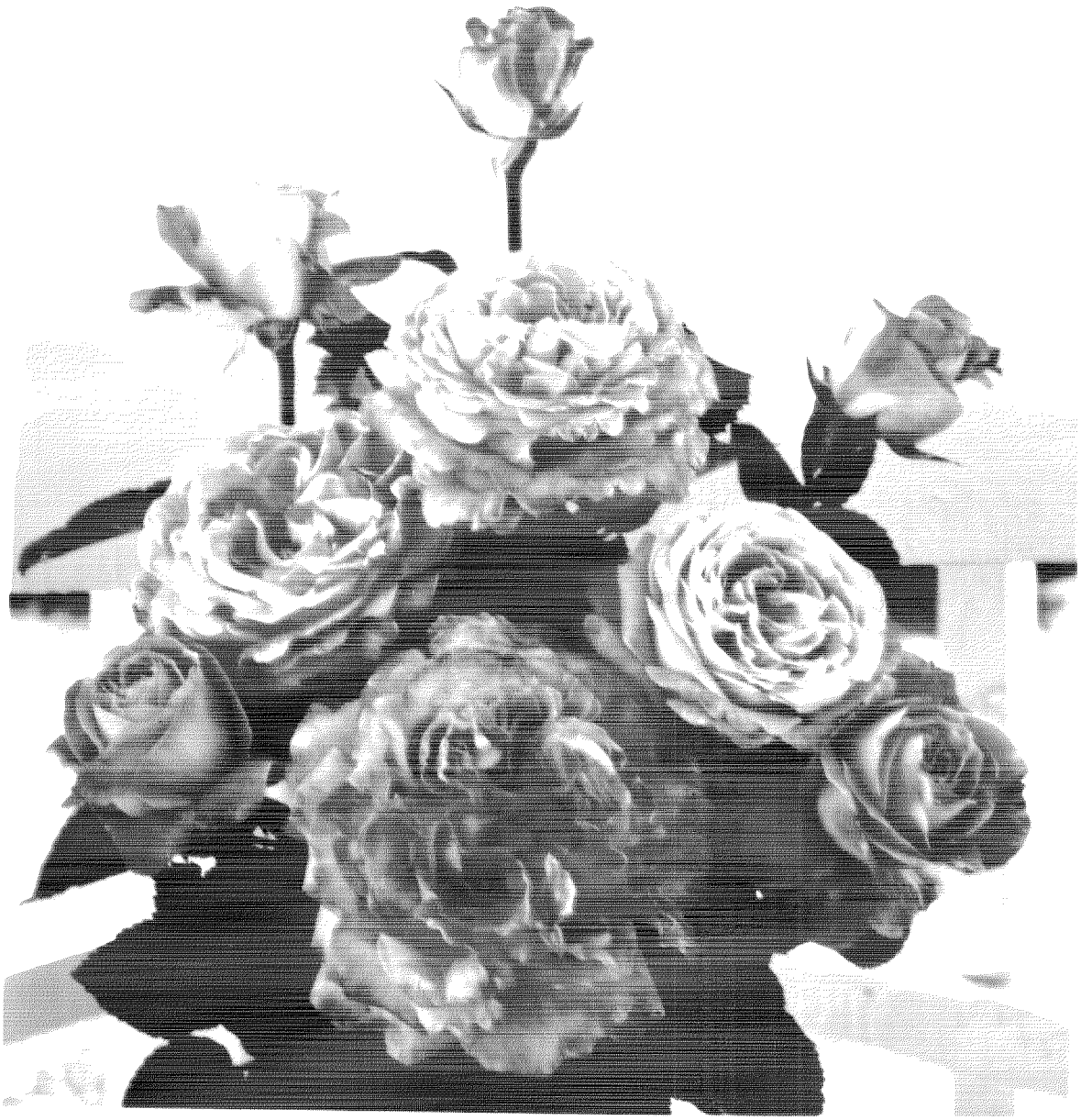

* * * * *